United States Patent [19]

Kobayashi et al.

[11] Patent Number: 5,268,286

[45] Date of Patent: Dec. 7, 1993

[54] METHOD FOR IMMOBILIZING BIOCATALYST IN GRANULAR FORM WITH A PHOTO-CROSSLINKABLE RESIN

[75] Inventors: Takeshi Kobayashi; Shinji Iijima; Masamichi Kamihira; Mikiko Hata, all of Nagoya; Takamitsu Iida, Hiratsuka; Masahiro Sakamoto, Naka; Hiroshi Itoh; Naoki Isobe, both of Utsunomiya, all of Japan

[73] Assignees: Ojo Kako Co., Ltd., Tokyo; Kansai Paint Co., Ltd., Hyogo, both of Japan

[21] Appl. No.: 665,360

[22] Filed: Mar. 6, 1991

[30] Foreign Application Priority Data

Mar. 9, 1990 [JP] Japan .................................. 2-56410

[51] Int. Cl.$^5$ ..................... C12N 11/10; C12N 11/12; C12N 11/08; C12N 11/04
[52] U.S. Cl. .................................. 435/178; 435/179; 435/180; 435/182
[58] Field of Search ................ 435/178, 179, 180, 182

[56] References Cited

U.S. PATENT DOCUMENTS

| | | | |
|---|---|---|---|
| 4,269,941 | 5/1981 | Ichimura | 435/180 X |
| 4,791,061 | 12/1988 | Sumino et al. | 435/178 |
| 5,051,362 | 9/1991 | Suehiro et al. | 435/182 |

Primary Examiner—David M. Naff
Attorney, Agent, or Firm—Leydig, Voit & Mayer

[57] ABSTRACT

A biocatalyst is immobilized with a graft product of a polymer and saponified polyvinyl acetate containing a stilbazolium group as a photo-crosslinking group. The polymer is preferably gelatin, collagen, starch, cellulose, gum arabic, tragacanth gum, carrageenan, mannan, dextrin or alginic acid. The graft product is prepared by bonding the polymer to the polyvinyl acetate, either directly through functional groups of the polymer and polyvinyl acetate or through a crosslinking agent. The polymer provides affinity for the biocatalyst and by grafting the polymer to the saponified polyvinyl acetate, damage to cells upon immobilization is reduced. A liquid composition containing a biocatalyst and the graft product is added to an aqueous solution of an inorganic salt or an organic salt to form a granular gel and the gel is irradiated with actinic rays to cure the gel.

20 Claims, No Drawings

METHOD FOR IMMOBILIZING BIOCATALYST IN GRANULAR FORM WITH A PHOTO-CROSSLINKABLE RESIN

BACKGROUND OF THE INVENTION

1. Field of the Invention

The present invention relates to a method of immobilizing a biocatalyst in the form of a granular formed body by using a water-dispersible photo-crosslinkable resin.

2. Description of the Related Art

As the biocatalyst to be immobilized, there can be mentioned animal cells, mammalian cells, plant cells, microbial cells and enzymes.

Attempts have been made to produce valuable substances by immobilizing biocatalysts by various polymers, but since the number of immobilizing polymers having a high affinity with biocatalysts is limited, a practical utilization of this technique is difficult.

The conventional technique will now be described, with reference to an animal cell as an example.

Intensive investigations have been made into the producing of many valuable substances by culturing animal cells in liquid culture media and some thereof have been industrially utilized.

As the method of culturing an animal cell, there can be mentioned not only a culturing method in which an animal cell is merely suspended in a liquid medium but also a gel entrapping immobilization culturing method in which an animal cell is entrapped in an aqueous gel and the immobilized cell is cultured in a liquid culture medium to effect a propagation of the cell in the gel. The latter method is advantageous in various points. For example, the animal cell which is mechanically weak or brittle against changes of the liquid properties can be protected by a gel layer during the culturing, and a solid-liquid separation between the cell and liquid, which is necessary for an exchange of the culture medium or recovery of the intended product after the culturing, can be performed very advantageously. Furthermore, an industrial production system can be easily established. For example, the intended substance can be continuously obtained by filling the gel which includes the immobilized cell in a bioreactor. Therefore, serious research has been made into materials for and methods of immobilizing animal cells.

Since animal cells are weak and brittle, natural substances such as alginic acid, carrageenan, mannan and gelatin are used as the immobilizing gel, but since the durability of the gel strength is poor, these gels are not industrially utilized, and research has been made with a view to improving the durability thereof. For example, there can be mentioned a method in which the kind of the salt is changed, to improve the durability of the gel strength at the entrapping immobilization of an animal cell with alginic acid, a method in which an animal cell-immobilizing gel is caused to flow in a reactor, to prevent a breaking of the gel, and a method in which, after the inclusion of an animal cell and an alginic acid gel, a synthetic polymer film is formed on the gel surface. Under this background, the development of a method in which a gel capable of entrapping an animal cell by an industrially applicable simple means, which can be used stably, can be formed, is urgently required.

SUMMARY OF THE INVENTION

It is therefore a primary object of the present invention to solve the foregoing problems of the conventional methods and provide a gel entrapping method in which an intended product is produced in a high yield over a long period without deactivation of cells in an animal cell colony formed by propagation in a gel.

In accordance with the present invention, there is provided a method of immobilizing a biocatalyst in a granular form, which comprises dropping a liquid composition comprising a graft product of a natural polymer and saponified polyvinyl acetate, containing a stilbazolium group as the photo-crosslinking group, and a biocatalyst into an aqueous medium containing an inorganic salt or an organic salt to gelatinize the liquid composition in the granular form, and irradiating the obtained granular gel with actinic rays to cure the photosensitive graft product of the natural polymer and saponified polyvinyl acetate.

DESCRIPTION OF THE PREFERRED EMBODIMENTS

The present invention will now be described in detail.

Preparation of Liquid Composition

The main skeleton of the stilbazolium photo-curable resin used in the present invention is a graft product of a natural polymer and saponified polyvinyl acetate. The introduction ratio of the natural polymer is preferably 1 to 2000 parts by weight per 100 parts by weight of saponified polyvinyl acetate.

As the natural polymer, there can be mentioned collagen, gelatin, casein, starch, cellulose, gum arabic, tragacanth gum, carrageenan, mannan, dextrin, alginic acid and derivatives of these natural polymers. Of these natural polymers, gelatin and collagen derived from animals are preferably used.

A natural polymer has an inherent good affinity with a biocatalyst, and by grafting the natural polymer to saponified polyvinyl acetate, damage to cells upon the immobilization of the biocatalyst can be reduced, and the propagation of the cell in a gel support by culturing greatly enhanced.

Accordingly, if the introduction ratio of the natural polymer is too low, the above effect is reduced, and if the introduction ratio of the natural polymer exceeds 2000 parts by weight, the content of saponified polyvinyl acetate is relatively reduced and the concentration of the stilbazolium group that can be added to saponified polyvinyl acetate is reduced, and therefore, the density of the photofunctional group is low at the formation of a gel by irradiation with actinic rays, and a biocatalyst-included gel having a high strength cannot be obtained.

As the method of grafting and integrating the natural polymer and saponified polyvinyl acetate, there can be adopted a method in which the natural polymer is directly bonded to saponified polyvinyl acetate by utilizing functional groups thereof, such as hydroxyl, carboxyl and amino groups, a method in which the natural polymer is bonded to saponified polyvinyl acetate by using a crosslinking agent such as glutaraldehyde, or a method in which a polymerizable monomer such as vinyl acetate is polymerized in the presence of a mixture of the natural polymer and saponified polyvinyl acetate, as the protecting colloid to effect the bonding integration indirectly.

The amount of the photo-crosslinking stilbazolium group to be added to the photo-curable resin is preferably 5 to 100 parts by weight per 100 parts by weight of saponified polyvinyl acetate contained in the graft product of the natural polymer and saponified polyvinyl acetate as the main skeleton of the photo-curable resin. If the addition ratio of the stilbazolium group is low, the ratio of reaction by irradiation with actinic rays is reduced, and therefore, the gel strength is reduced and unreacted low-molecular-weight resin composition remains in the gel and has an adverse influence on the entrapped biocatalyst. If the addition ratio of the stilbazolium group is too high, the properties of the photo-curable resin are changed and an economical disadvantage arises.

The thus-synthesized stilbazolium type photo-curable resin can be purified by solvent fractionation or can be directly used for the immobilization of the biocatalyst. When the solvent fractionation or the like is adopted, it is necessary to sufficiently remove the used solvent so that the solvent does not remain in the photo-curable resin, and an adverse influence cannot be imposed on the biocatalyst.

The kind of the biocatalyst that can be immobilized according to the method of the present invention is not particularly critical, and as the biocatalyst, there can be mentioned animal cells, mammalian cells, plant cells, microbial cells and enzymes. Normal cells and tumor cells can be used as the animal and plant cells, or hybridoma having an enhanced substance productivity of cells per se by cell fusion, cell technology or genetic engineering can be used. As the microbial cell, there can be used yeasts, bacteria, molds, actinomycetes, basidiomycetes and all of other microorganisms. As specific examples of the yeast, there can be mentioned baker's yeast, wine yeast, sake yeast, *Shizosaccharomyces pombe* and *Rhodotorula clutinis*.

As the enzyme, there can be mentioned, for example, hydrolases such as amylase, protease, cellulase, hemicellulase, lipase, pectinase, lysozyme, naringenase, hesperidinase, anthocyanase, aminoacylase, urease, invertase, melibiase, dextrase, peptitase, ribonuclease and lactase, oxidoreductases such as glucose oxidase, uricase, catalase, lipoxygenase and cytochrome c peroxidase, isomerases such as glucose isomerase, transferases such as cyclodextrin glucocyl transferase and transaminase, and lyases such as aspartase, hyaluronidase, chondroitinase and pectin eliminase.

A liquid composition is prepared by mixing a biocatalyst as mentioned above with the stilbazolium type photocurable resin. An aqueous solution of sodium alginate can be added to the liquid composition, whereby an effect of enhancing the granule-forming property can be attained when the liquid composition is dropped into an aqueous medium containing a salt. The amount added of sodium alginate is preferably 1 to 50% based on the solids of the photo-curable resin. The cell concentration in the initial biocatalyst in the thus-obtained liquid composition is preferably $10^4$ to $10^7$ cells/ml.

Granulation

The liquid composition prepared from the graft product of the natural polymer and saponified polyvinyl acetate, in which the stilbazolium group is introduced as the photo-crosslinking group, and the biocatalyst is dropped into an aqueous medium containing an inorganic salt or organic salt, whereby the liquid composition is gelatinized in the granular form.

If the inorganic or organic salt is present in the aqueous medium at a concentration of 0.001 to 5 moles/l, preferably 0.05 to 0.5 mole/l, the kind or valency of the salt is not particularly critical.

As specific examples of the inorganic salt, there can be mentioned halides, carbonates, bicarbonates, sulfates and nitrates of alkali metals such as sodium and potassium, alkaline earth metals such as calcium and barium, aluminum and trivalent iron; among these, alkali metal salts are preferably used. These inorganic salts can be used alone or in the form of a mixture of two or more thereof. Furthermore, natural sea water or artificial sea water can be used.

As specific examples of the organic salt, there can be mentioned onium salts such as tetra-n-butyl ammonium bromide, and aniline hydrochloride, piperidine hydrochloride, hydrazine sulfate and phenylhydrazine sulfate.

Where a liquid composition comprising the photo-crosslinkable graft product of the natural polymer and saponified polyvinyl acetate, sodium alginate and the biocatalyst is dropped into an aqueous medium containing an inorganic salt to gelatinize the liquid composition into the granular form, an aqueous medium containing an inorganic salt as mentioned above can be used, and an alkaline earth metal salt is preferably used.

Dropping of the above-mentioned liquid composition into an aqueous medium containing an inorganic or organic salt as mentioned above is accomplished, for example, by a method in which the liquid composition is dropped from the top end of a tube having a sharp edge, such as a hydermic needle, a method in which the liquid composition is scattered in the form of granules by utilizing the centrifugal force, or a method in which the liquid composition is atomized from the top end of a spray nozzle. The size of drops of the liquid composition can be changed according to the particle size desired for the final granular immobilization product, but for the reasons set forth above, the diameter of the liquid drops is preferably 0.5 to 5 mm.

Instead of the method of immobilizing the biocatalyst on the granulation immobilization carrier, there can be effectively adopted a method in which the biocatalyst is immobilized on a membrane comprising the graft product of the natural polymer and saponified polyvinyl acetate having the stilbazolium group as the photo-crosslinking group according to the present invention.

Photo-curine

If the thus-formed granular gel is irradiated with actinic rays while dispersed in the aqueous medium or separated therefrom, crosslinking-curing is accomplished by the stilbazolium group added to the grafting product of the natural polymer and saponified polyvinyl acetate contained in the granular gel, whereby the granular gel is converted to a water-soluble granular immobilization product.

Preferably, the wavelength of the actinic rays used for the photo-curing is in a region not imposing an adverse influence on the biocatalyst. Namely, rays having a wavelength shorter than about 320 nm are preferably eliminated. As examples of the light sources emitting such rays, there can be mentioned a low-pressure mercury lamp, a high-pressure mercury lamp, a fluorescent lamp, a xenon lamp, and sunlight. The irradiation time should be changed according to the ray intensity of the light source, the distance from the light source and the like, but in general, the irradiation time can be 1 to 5 minutes. Furthermore, the actinic rays must be applied to the formed granular gel as uniformly as possible.

After the irradiation treatment, the treated granular gel can be washed with water or an aqueous buffer solution and then stored, or can be directly used for culturing.

EXAMPLES

The present invention will now be described in detail with reference to the following examples, that by no means limit the scope of the invention.

EXAMPLE 1

In 100 g of an aqueous solution of an emulsion of polyvinyl acetate obtained by polymerizing vinyl acetate according to customary procedures by using, as the protecting colloid, a mixture of gelatin [jelly strength (6.66% aqueous solution) of 259 g, viscosity (6.66% aqueous solution) of 42 mps, molecular weight of 100,000] and saponified polyvinyl acetate (saponification degree of 88 mole %, polymerization degree of 1400) was dissolved 2 g of N-methyl-4-(p-formylstyryl)-pyridinium methosulfate, and addition condensation was carried out to synthesize a photosensitive emulsion. In the polyvinyl acetate emulsion aqueous solution, the gelatin/saponified polyvinyl acetate weight ratio was 15/85, the solid weight ratio of the protecting colloid in the total solids was 50%, and the solid concentration was 15%. To 20 parts by weight of the photosensitive emulsion was added 10 parts by weight of a cell suspension of PRM18204 derived from human leukocytes to form a liquid mixture having a cell concentration of $7 \times 10^5$ cells/ml. The liquid mixture was charged into a syringe and was dropped into a 0.05M aqueous solution of sodium chloride while shaking the syringe, whereby granulation was effected. Then, the mixture was irradiated with rays having a main wavelength of 300 to 400 nm for 2 minutes to obtain a granular gel having a particle size of 1.5 mm. Thereafter, twenty immobilized animal cells were sampled and added to 10 ml of a culture medium formed by adding 10% of FCS to a PRM11640 culture medium, and culturing was conducted at 37° C. When the culturing was carried out for 2 days, the glucose concentration in the culture medium was reduced to 0.8 g/l from 1.8 g/l.

Example 2

To 20 parts by weight of the photosensitive emulsion prepared in Example 1 was added 40 parts by weight of a 1% aqueous solution of sodium alginate, and monoclonal antibody-producing mouse hybridoma strain 16-3F was added to the mixed resin liquid to form a liquid mixture having a cell concentration of $2 \times 10^6$ cells/ml. The liquid mixture was dropped into a 0.1M aqueous solution of potassium chloride from a syringe to effect granulation. The liquid mixture was irradiated with rays having a main wavelength of 300 to 400 nm. The formed granular immobilized cells were transferred into a 0.1M aqueous solution of sodium citrate and stored in a refrigerator overnight. Then, 24 granular immobilized cells were sampled and added to 8 ml of DF/ITES culture medium, and exchange of the culture medium was performed every other day. After 22 days' culturing, the cell concentration in the granular gel became $1 \times 10^7$/ml of the gel, and the antibody value of the obtained culture liquid was 200.

Comparative Example 1

A photosensitive emulsion was synthesized by dissolving 2 g of N-methyl-4-(p-formylstyryl)pyridinium methosulfate in 100 g of an aqueous solution of an emulsion of polyvinyl acetate formed according to customary procedures by polymerizing vinyl acetate in the presence of saponified polyvinyl acetate (saponification degree of 88 mole %, polymerization degree of 1400) as the protecting colloid [the solid weight ratio of the protecting colloid based on the total solids was 50% and the solid concentration was 15%] and carrying out the addition condensation according to customary procedures. To 20 parts by weight of the photosensitive emulsion was added 10 parts by weight of a cell suspension of PRM18204 derived from human leukocytes to form a liquid mixture having a cell concentration of $7 \times 10^5$ cells/ml. The liquid mixture was charged in a syringe and dropped into a 0.05M aqueous solution of sodium chloride while shaking the syringe, whereby granulation was effected. The liquid mixture was irradiated with rays having a main wavelength of 300 to 400 nm for 2 minutes to obtain a granular gel having a particle size of 1.5 mm. Then, 20 immobilized animal cells were sampled and added to 10 ml of a culture medium formed by adding 10% of FCS to RPM11640 culture medium and culturing was conducted at 37° C. Even when culturing was carried out for 2 days, the glucose concentration in the culture medium was little changed from the initial level of 1.8 g/l.

Comparative Example 2

In 100 g of an aqueous solution of an emulsion of polyvinyl acetate obtained by polymerizing vinyl acetate according to customary procedures by using as the protecting colloid the same gelatin as used in Example 1 (the solid weight ratio of the protecting colloid to the total solids was 50% and the solid concentration was 15%) was dissolved 2 g of N-methyl-4-(p-formylstyryl)-pyridinium methosulfate, and the addition condensation was carried out according to customary procedures. The reaction liquid had no photo-crosslinkability.

Comparative Example 3

A 2% aqueous solution of sodium alginate was dropped into an aqueous medium containing 1% of potassium chloride from a hypodermic needle to form a granular gel having a diameter of about 2 mm. A bioreactor having an inner volume of 100 ml, into which germ-free air could be introduced from the bottom, was charged with 70 ml of BME culture medium, and about 10 ml of the granular gel was added into the reactor and fluidized by aeration. When the gel was fluidized at a temperature of 37° C. for 24 hours, the granular gel was dissolved in the BME culture medium.

I claim:

1. A method of immobilizing a biocatalyst in a granular form, which comprises adding a liquid composition comprising a biocatalyst and a graft product formed by banding together (a) a polymer selected from the group consisting of collagen, gelatin, casein, starch, cellulose, gum arabic, tragacanth gum, carrageenan, mannan, dextrin, alginic acid, derivatives of collagen, derivatives of gelatin, derivatives of casein, derivatives of starch, derivatives of cellulose, derivatives of gum arabic, derivatives of tragacanth gum, derivatives of carrageenan, derivatives of mannan, derivatives of dextrin, and derivatives of alginic acid and (b) saponified polyvinyl acetate containing a stilbazolium group as a photo-crosslinking group, said polymer being present in an amount from about 1% to about 2000% by weight of said saponified polyvinyl acetate, to an aqueous medium containing an inorganic salt or an organic salt to gelatinize said liquid composition in the granular form, and irradiating the obtained granular gel with actinic rays to cure said gel.

2. The method according to claim 1, wherein the liquid composition further comprises sodium alginate in addition to said biocatalyst, said polymer, and said saponified polyvinyl acetate.

3. The method according to claim 2, wherein said sodium alginate is present in an amount from about 1% to about 50% based on the solids of the graft product.

4. The method according to claim 1, wherein the graft product is formed by the direct bonding of the polymer and saponified polyvinyl acetate through functional groups thereof.

5. The method according to claim 4, wherein the functional groups are selected from the group consisting of hydroxyl, carboxyl and amino.

6. The method according to claim 1, wherein the graft product is formed by the bonding of the polymer and saponified polyvinyl acetate through a crosslinking agent.

7. The method according to claim 6, wherein the crosslinking agent is glutaraldehyde.

8. The method according to claim 1, wherein the graft product is formed by the polymerization of a polymerizable monomer in a mixture of the polymer and saponified polyvinyl acetate.

9. The method according to claim 8, wherein the polymerizable monomer is vinyl acetate.

10. The method according to claim 1, wherein the photo-crosslinking stilbazolium group is present in an amount from about 5% to about 100% by weight of saponified polyvinyl acetate.

11. The method according to claim 1, wherein the biocatalyst is selected from the group consisting of animal cells, mammalian cells, plant cells, microbial cells and enzymes.

12. The method according to claim 11, wherein the microbial cells are selected from the group consisting of yeasts, bacteria, molds, actinomycetes and basidiomycetes.

13. The method according to claim 11, wherein the enzymes are selected from the group consisting of hydrolases, oxidoreductases, isomerases, transferases and lyases.

14. The method according to claim 1, wherein the biocatalyst is present in the liquid composition in a concentration of from about $10^4$ to about $10^7$ cells/ml.

15. The method according to claim 1, wherein the inorganic or organic salt is present in the aqueous medium in a concentration of 0.001 to 5 moles/l.

16. The method according to claim 1, wherein the inorganic salt is selected from the group consisting of halides, carbonates, bicarbonates, sulfates and nitrates of alkali metals and alkaline earth metals.

17. The method according to claim 1, wherein the organic salts are selected from the group consisting of onium salts, aniline hydrochloride, piperidine hydrochloride, hydrazine sulfate and phenylhydrazine sulfate.

18. The method according to claim 1, wherein the gel is cured by irradiating the gel with actinic rays while the gel is still dispersed in the aqueous medium.

19. The method according to claim 1, wherein the gel is cured by irradiating the gel with actinic rays after the gel has been separated from the aqueous medium.

20. The method according to claim 11, wherein the irradiation is carried out using a light source selected from the group consisting of a low-pressure mercury lamp, high-pressure mercury lamp, fluorescent lamp, xenon lamp and sunlight.

* * * * *